(12) United States Patent
Hinshon

(10) Patent No.: US 11,278,439 B2
(45) Date of Patent: Mar. 22, 2022

(54) ANKLE-FOOT ORTHOSIS

(71) Applicant: Orthotic Care Services, LLP, Minneapolis, MN (US)

(72) Inventor: Patrick Scott Hinshon, Maplewood, MN (US)

(73) Assignee: Orthotic Care Services, LLP, Minneapolis, MN (US)

(*) Notice: Subject to any disclaimer, the term of this patent is extended or adjusted under 35 U.S.C. 154(b) by 982 days.

(21) Appl. No.: 15/063,079

(22) Filed: Mar. 7, 2016

(65) Prior Publication Data

US 2017/0252197 A1 Sep. 7, 2017

(51) Int. Cl.
*A61F 5/01* (2006.01)

(52) U.S. Cl.
CPC .... *A61F 5/0127* (2013.01); *A61F 2005/0137* (2013.01); *A61F 2005/0169* (2013.01)

(58) Field of Classification Search
CPC ........... A61F 5/0111; A61F 2005/0137; A61F 5/0102; A61F 5/058; A61F 5/0195; A61F 5/01; A61F 5/0585; A61F 5/0113; A61F 5/0127; A43B 1/00; A43B 1/14; A43B 1/04; A43B 7/14; A43B 7/28; A43B 7/20; A43B 7/141; A43B 7/00; A43B 5/1691; A43B 5/0405; A43B 5/0419; A43B 5/047; A43B 5/04; A61H 1/0237; A61H 1/0266
USPC .... 602/5, 16, 23, 27, 12, 28; 36/1.5, 83, 84, 36/85, 87, 88, 89, 93, 102, 110, 117.4, 36/117.5, 117.6, 140; 128/882; 601/27, 601/33; 2/22
See application file for complete search history.

(56) References Cited

U.S. PATENT DOCUMENTS

| | | | |
|---|---|---|---|
| 3,896,502 A | 7/1975 | Lennox | |
| 3,896,503 A | 7/1975 | Freeman et al. | |
| 4,289,122 A | 9/1981 | Mason et al. | |
| D286,183 S | 10/1986 | Womack et al. | |
| 4,665,904 A | 3/1987 | Lerman | |
| 4,693,239 A | 9/1987 | Clover, Jr. | |
| D297,368 S | 8/1988 | Womak | |
| 4,771,768 A | 9/1988 | Crispin | |
| 4,869,267 A * | 9/1989 | Grim | A43B 7/20 602/27 |
| 4,974,583 A | 12/1990 | Freitas | |
| D316,150 S | 4/1991 | Day et al. | |
| 5,022,390 A | 6/1991 | Whiteside | |
| 5,066,305 A | 11/1991 | Firth | |
| 5,326,364 A | 7/1994 | Clift, Jr. et al. | |
| 5,328,444 A | 7/1994 | Whiteside | |
| 5,501,659 A | 3/1996 | Morris et al. | |

(Continued)

FOREIGN PATENT DOCUMENTS

| | | |
|---|---|---|
| EP | 1374810 A1 | 1/2004 |
| FR | 2827158 A1 | 1/2003 |

(Continued)

*Primary Examiner* — Caitlin A Carreiro
(74) *Attorney, Agent, or Firm* — Craig J. Lervick; Larkin Hoffman Daly & Lindgren, Ltd.

(57) ABSTRACT

An ankle-foot orthosis having an articulated outer boot adapted to provide support and limit plantar-flexion, and a cooperating inner boot adapted to facilitate transition from mid-stance phase to terminal contact phase of the gait cycle. The ankle-foot orthosis of the present invention can provide lower-limb alignment while delivering power assistance to achieve normal swing phase.

13 Claims, 14 Drawing Sheets

(56) References Cited

U.S. PATENT DOCUMENTS

| | | |
|---|---|---|
| 5,545,127 A | 8/1996 | DeToro |
| D385,358 S | 10/1997 | Carlson |
| 5,716,336 A | 2/1998 | Hines et al. |
| 5,799,659 A | 9/1998 | Stano |
| 5,826,304 A | 10/1998 | Carlson |
| 5,853,380 A | 12/1998 | Miller |
| 5,897,514 A | 4/1999 | Currier |
| 5,944,679 A | 8/1999 | DeToro |
| 5,961,477 A | 10/1999 | Turtzo |
| 6,207,092 B1 | 3/2001 | Kulkaski |
| 6,355,335 B1 | 3/2002 | Kulkaski |
| 6,409,695 B1 | 6/2002 | Connelly |
| 6,447,889 B2 | 9/2002 | Kulkaski |
| D487,512 S | 3/2004 | Bradshaw et al. |
| 6,787,223 B2 | 9/2004 | Warren |
| 6,824,523 B2 | 11/2004 | Carlson |
| 6,827,696 B1 | 12/2004 | Maguire |
| 6,860,864 B2 | 3/2005 | Meyer |
| 6,929,614 B1 | 8/2005 | Jackovitch |
| 6,945,946 B2 | 9/2005 | Rooney |
| 7,018,350 B2 | 3/2006 | Hinshon |
| 7,018,352 B2 | 3/2006 | Pressman et al. |
| 7,044,926 B2 | 5/2006 | Carlson |
| 7,112,180 B2 | 9/2006 | Guenther |
| 7,182,743 B2 | 2/2007 | Slautterback et al. |
| 7,270,644 B2 | 9/2007 | Ingimundarson |
| 7,335,177 B2 | 2/2008 | Reynolds et al. |
| 7,468,004 B2 | 12/2008 | Kim |
| 7,476,208 B1 * | 1/2009 | Shirley ............... A61F 5/0111 602/23 |
| D596,301 S | 7/2009 | Campos et al. |
| 7,572,241 B2 | 8/2009 | Slautterback et al. |
| 7,678,067 B1 | 3/2010 | Smith et al. |
| 7,682,322 B2 | 3/2010 | Engelman |
| 7,753,866 B2 | 7/2010 | Jackovitch |
| 7,896,828 B1 | 3/2011 | Shirely |
| 7,967,768 B2 | 6/2011 | Watts |
| 8,007,456 B2 | 8/2011 | Stano |
| 8,251,935 B2 | 8/2012 | Bonutti et al. |
| 8,282,588 B2 | 10/2012 | Ingimundarson et al. |
| 8,328,745 B2 | 12/2012 | Einarsson et al. |
| D693,471 S | 11/2013 | Bradshaw |
| 8,584,430 B2 | 11/2013 | Tarr |
| 9,022,762 B2 | 5/2015 | Yao |
| 9,078,735 B2 | 7/2015 | Perkins |
| 9,168,166 B2 | 10/2015 | Bradshaw |
| 9,168,270 B2 | 11/2015 | Blanck |
| 9,192,502 B2 | 11/2015 | Drillio |
| 2003/0125653 A1 | 7/2003 | Meyer |
| 2003/0153852 A1 | 8/2003 | Hinshon |
| 2003/0153859 A1 | 8/2003 | Hinshon |
| 2003/0158506 A1 | 8/2003 | Hinshon |
| 2011/0196276 A1 * | 8/2011 | Kuhn ............... A61F 5/0127 602/27 |
| 2012/0310121 A1 | 12/2012 | Bonutti et al. |
| 2013/0000245 A1 | 1/2013 | Tarr |
| 2014/0213953 A1 * | 7/2014 | Heyd ............... A61F 5/0104 602/27 |
| 2014/0257162 A1 | 9/2014 | Falkenman et al. |
| 2014/0276314 A1 * | 9/2014 | Heyd ............... A61F 5/0111 602/27 |
| 2014/0288475 A1 | 9/2014 | Watts |
| 2015/0094637 A1 | 4/2015 | Schwartz |

FOREIGN PATENT DOCUMENTS

| | | |
|---|---|---|
| GB | 2420716 A | 6/2006 |
| WO | 2003063730 A2 | 8/2003 |
| WO | 2004066890 A1 | 8/2004 |
| WO | 2011137999 A1 | 11/2011 |
| WO | 2011141283 A1 | 11/2011 |

* cited by examiner

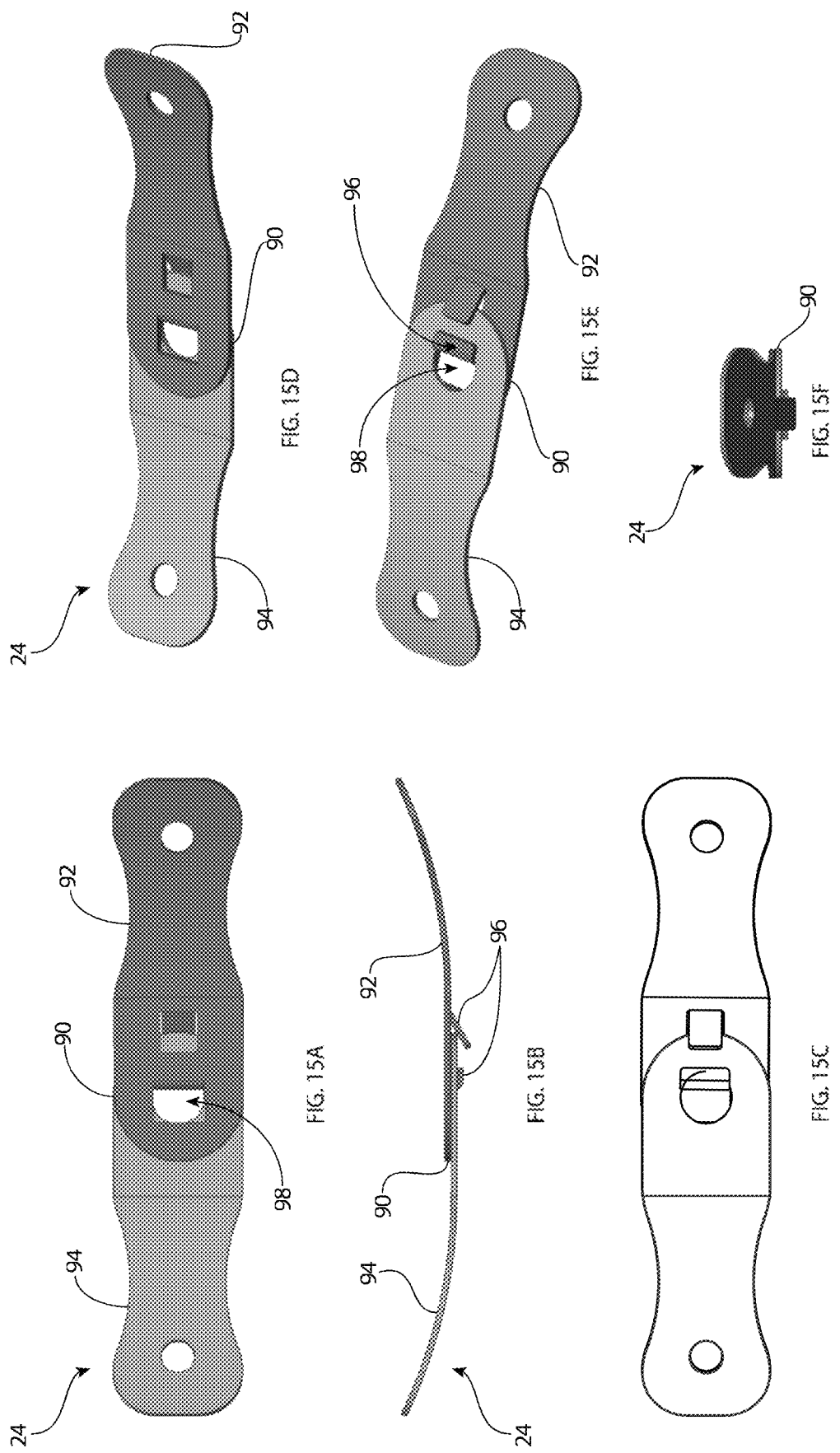

ANKLE-FOOT ORTHOSIS

FIELD OF THE INVENTION

The present invention relates generally to orthoses and, more particularly, to ankle-foot orthoses.

BACKGROUND

An orthosis is an externally applied mechanical or electromechanical device used to modify the structural and functional characteristics of a patient's neuromuscular and/or skeletal system. Orthoses can be used to aid individuals who suffer the physiological effects resulting from many different events, conditions and/or ailments, such as trauma, disease, genetic disorder or neurological impairment such as stroke, spinal cord injury and peripheral neuropathy. Specifically, orthoses can be used to control and/or restrict movement in a given direction, assist movement, reduce weight-bearing forces, correct the shape and function of portions of the body, facilitate movement generally and control, guide, limit or immobilize a joint or extremity.

An orthosis is customarily adapted for a particular anatomical region. Upper-extremity orthoses, for example, can be used to restore or improve the function or structural characteristics of the arm segments of an individual. Similarly, lower-extremity orthoses are applied to lower-body joints and limbs. Lower-extremity orthoses are frequently used to assist an individual with walking by stabilizing gait, transferring loads and correcting or preventing the progression of deformities.

Lower-extremity orthoses include foot orthoses, knee orthoses, ankle-foot orthoses (also known as AFOs) and knee-ankle-foot orthoses. Among these types of lower-limb orthoses, AFOs are particularly useful for assisting individuals affected by injury, abnormality or other adverse condition in or around the lower leg, ankle and foot. As known, the function of the ankle-foot is very complex, providing stability, strength and accommodating a wide variety of physical activities.

An AFO is typically designed to deal with at least one condition which is creating problems. For example, foot drop (also known as drop foot) is a gait abnormality characterized by the inability or impaired ability to raise the forefoot from the ankle (dorsiflexion). Foot drop may be temporary or permanent depending upon the cause, which can include nerve damage, muscle trauma, anatomical abnormalities, disease or toxins.

Individuals with foot drop, or drop-foot individuals, tend to drag their toes along the ground while walking. To avoid this, many drop-foot individuals alter their gait by exaggerating the phases of normal gait cycle. Specifically, during swing phase of the gait cycle (the period in the gait cycle when the foot is not in contact with the ground), a drop-foot individual will raise his or her knee higher to accommodate the inability to dorsiflex. This exaggerated motion provides clearance for the individual's foot above the ground surface, but also effectuates a stair-climbing movement.

During first rocker phase (the period in the gait cycle, when the foot initially makes contact with the ground surface), the foot of a drop-foot individual will often slap the ground surface or be planted all at once rather than achieve a normal heel-toe foot strike. During third rocker phase, a drop-foot individual may not be able to support his or her body weight. In addition, the individual is not able to push off or extend his or her foot during the third rocker phase. As recognized, this extension is required for any running or jumping activities. As such, it can be beneficial to provide dorsiflexion assistance in the third rocker phase as the foot is lifted from the ground surface.

AFOs can ameliorate drop foot and other adverse conditions by limiting the range of downward extension of a foot away from the leg (plantar flexion). For example, many AFOs are made from a rigid or semi-rigid material that resists deformation of the AFO within the plane of dorsiflexion/plantar flexion (i.e., the sagittal plane). Other AFOs incorporate a mechanical stop designed to prevent plantar flexion beyond a pre-determined angle.

Despite their advantages, existing plantar flexion-limiting AFOs have a number of drawbacks, such as excessive rigidity resulting in unintended muscle atrophy and undesirable operational characteristics. This includes, in part, insufficient or absence of dorsiflexion resistance during terminal contact of the third rocker phase as the foot is lifted from the ground surface. For example, using an articulated AFO to provide dorsiflexion assistance inherently requires a plantar flexion stop in order to block functional/active plantar flexion. Blocking plantar flexion, however, creates a deficit at the third rocker (terminal stance) phase that prevents the ankle from breaking a ninety degree (90°) angled in the sagittal plane. Decreasing the range of motion in turn decreases the power needed to effect push-off from the terminal stance and promote adequate step length on the contralateral side.

SUMMARY

Embodiments of the ankle-foot orthosis of the present invention substantially meet the aforementioned needs. In an embodiment, the ankle-foot orthosis includes an outer boot and an inner boot. The outer boot includes an upper portion coupled to a lower portion. Each of the upper and lower portions includes a tensioner. The outer boot may also include a plantar flexion stop and a hinge coupling the upper portion to the lower portion. Upper and lower portions of the outer boot are made from a substantially stiff material, whereas the inner boot is made from a substantially flexible material.

In an embodiment, the outer boot substantially supports, and the inner boot substantially conforms to, the foot-ankle joint and part the lower-leg region of a user. In particular, the inherent stiffness of the outer boot inhibits torsion of a foot within the transverse, or coronal, plane, while a hinge and/or joint permits flexion in the sagittal plane about the axis defined by the user's ankle. Tensioners impede buckling of the inner boot during dorsiflexion. The hinges and/or joints enhance cooperation between the upper and lower portions of the outer boot to provide functionality and enhanced comfort. In addition, the upper and lower portions of the outer boot can be tailored to provide customized levels of therapy and support to a user.

The shape and inherent elasticity of the inner boot, as well as the foot plate of the outer boot, facilitate energy storage during dorsiflexion as the user transitions through stance phase from second rocker to third rocker. This stored energy can then be released during plantar flexion to facilitate the transition from stance phase to swing phase. By effectively enhancing step length, the AFO of the present invention helps to the user to achieve a substantially normal gait cycle.

BRIEF DESCRIPTION OF THE DRAWINGS

FIG. 15A is a top plan view of a joint for an ankle-foot orthosis;

FIG. 15B is a side view of the joint illustrated in FIG. 15A;

FIG. 15C is a bottom plan view of the joint illustrated in FIG. 15A;

FIG. 15D is a top perspective view of the joint illustrated in FIG. 15A;

FIG. 15E is a bottom perspective view of the joint illustrated in FIG. 15A; and

FIG. 15F is a front elevation view of the joint illustrated in FIG. 15A.

DESCRIPTION OF THE PREFERRED EMBODIMENTS

An ankle-foot orthosis (or AFO) 10 is depicted generally in FIGS. 1-4. Although AFO 10 can be used for any number of purposes, the illustrated embodiments are especially suitable for use as an orthotic device to assist with walking, as generally shown in FIGS. 14A-D. AFO 10 may be particularly suitable for counteracting foot drop while facilitating foot lift during the gait cycle. Though AFO 10 can be used to provide assistance during swing phase, the combination of hinged outer boot made of a relatively harder material and an interior boot made of a substantially softer, more elastic material allows AFO 10 to provide assistance during stance phase as well.

Figure 2:
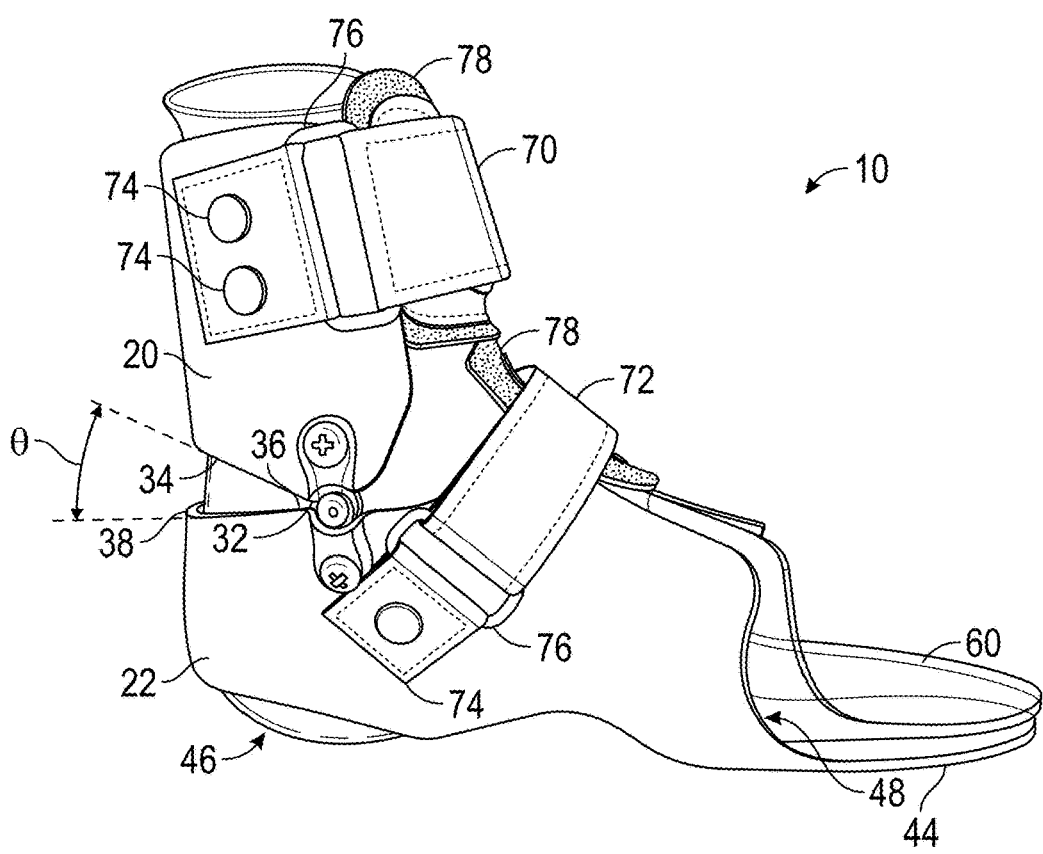
FIG. 2 is a side view of an embodiment of an ankle-foot orthosis.
Figure 3:
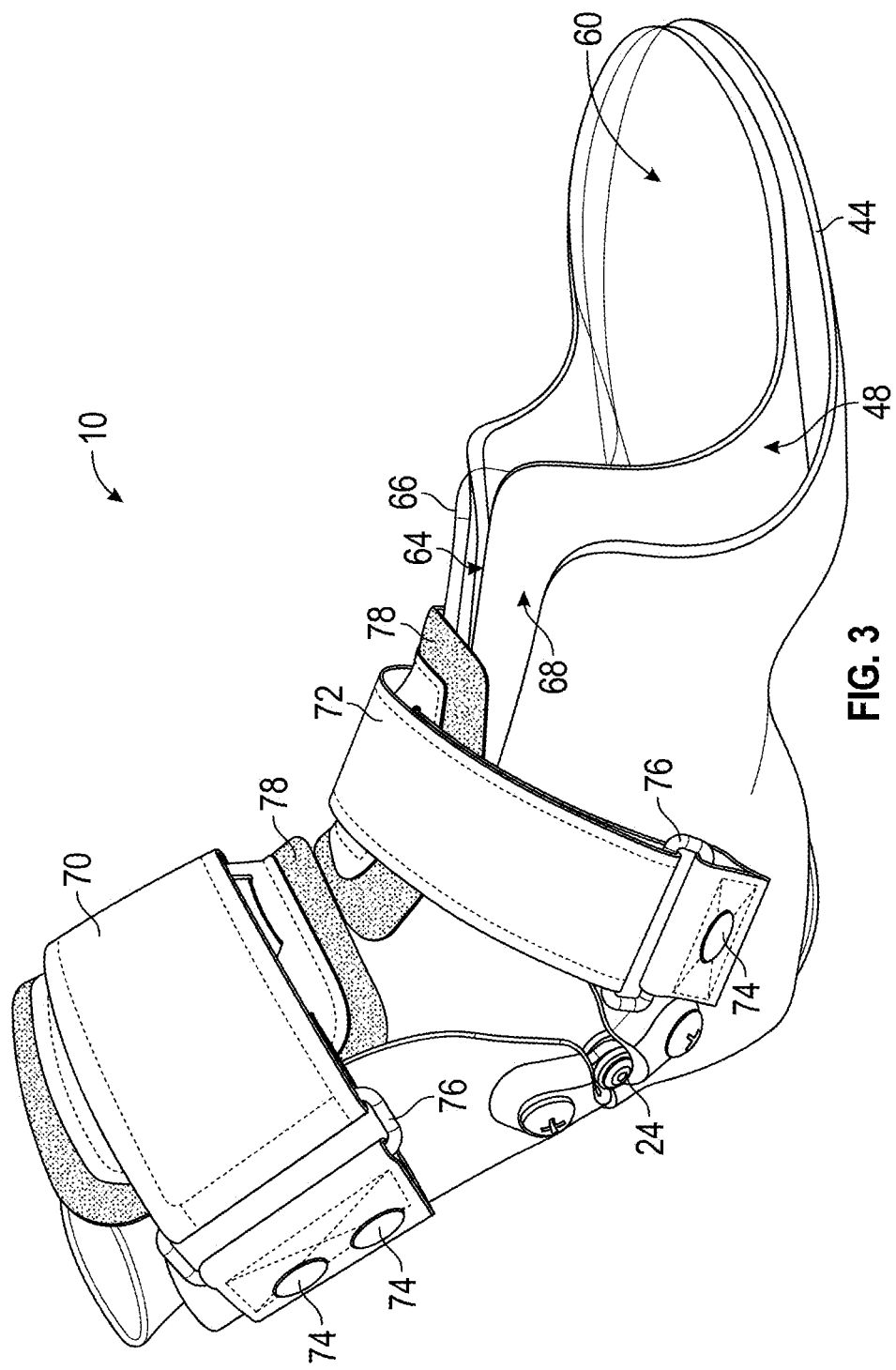
FIG. 3 is a front perspective view of the ankle-foot orthosis illustrated in FIG. 2.
Figure 4:
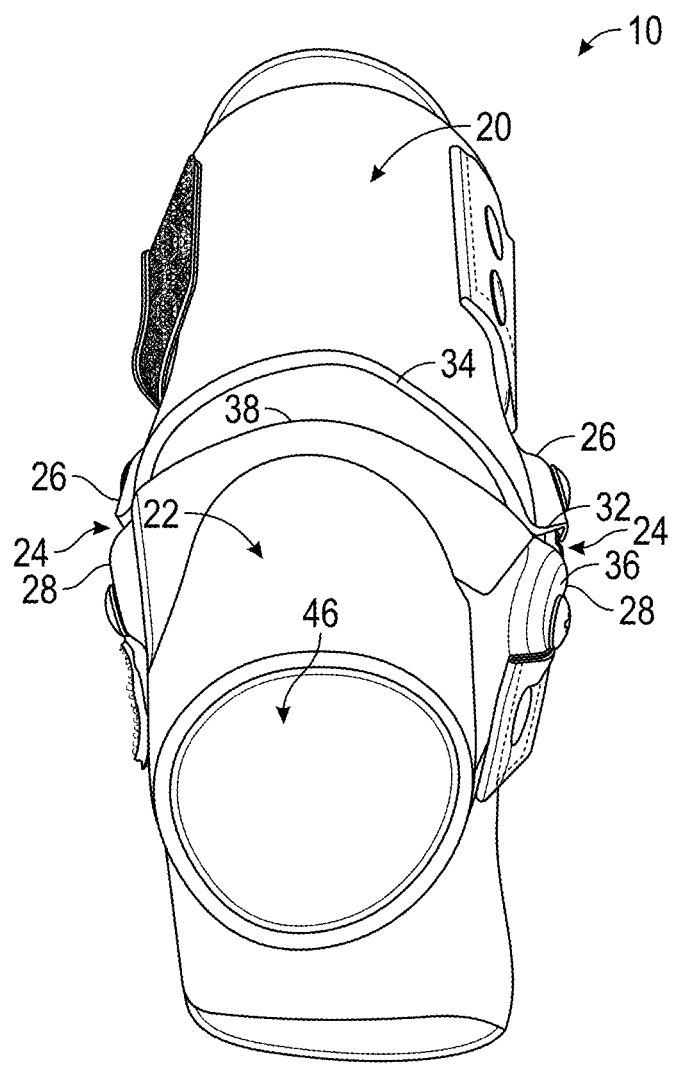
FIG. 4 is a rear perspective view of the ankle-foot orthosis illustrated in FIG. 2.
Figure 5:
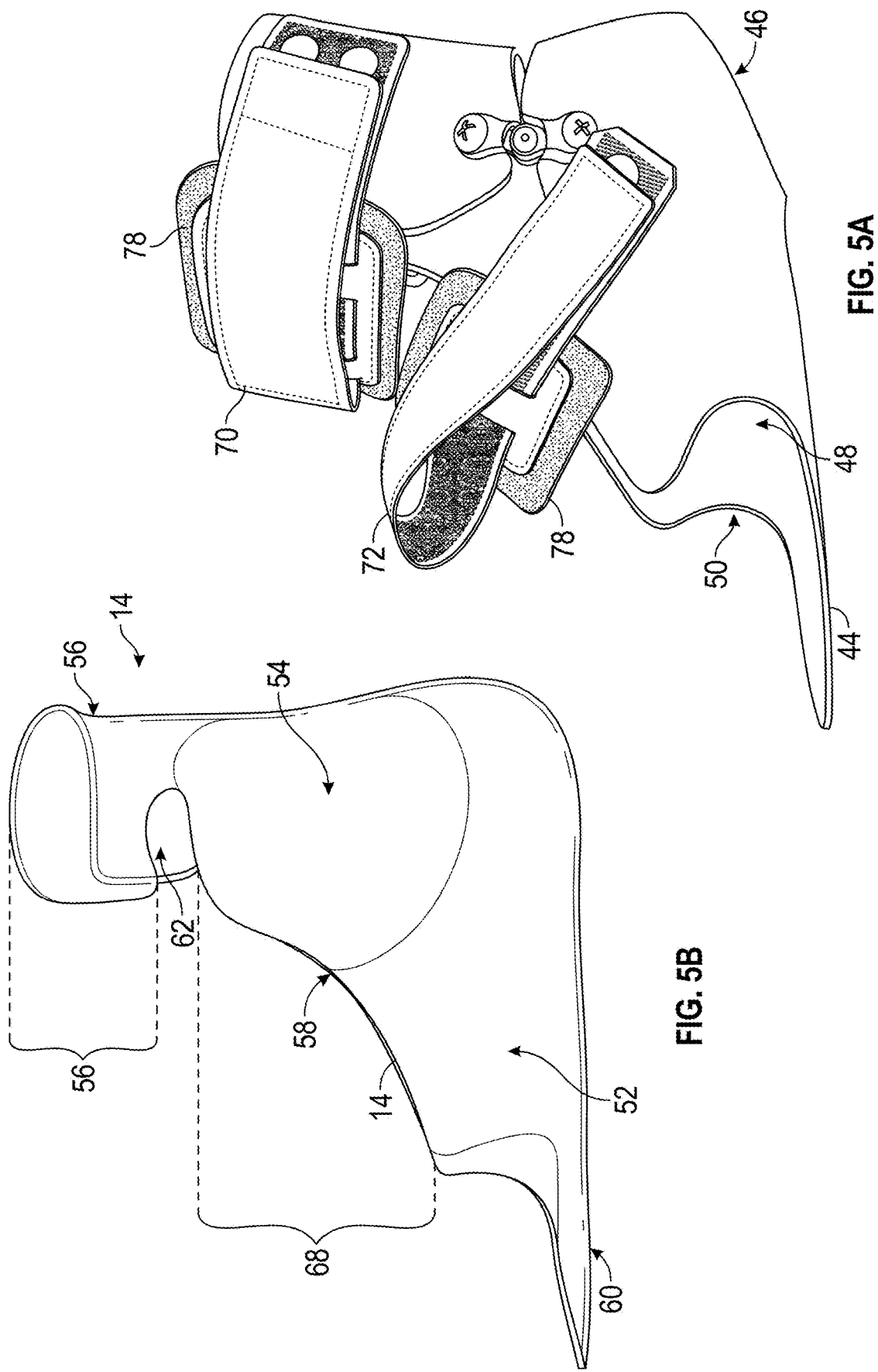
FIG. 5A is a side view of an outer boot of the ankle-foot orthosis illustrated in FIG. 2.
FIG. 5B is a side view of an inner boot of the ankle-foot orthosis illustrated in FIG. 2.
Figure 6:
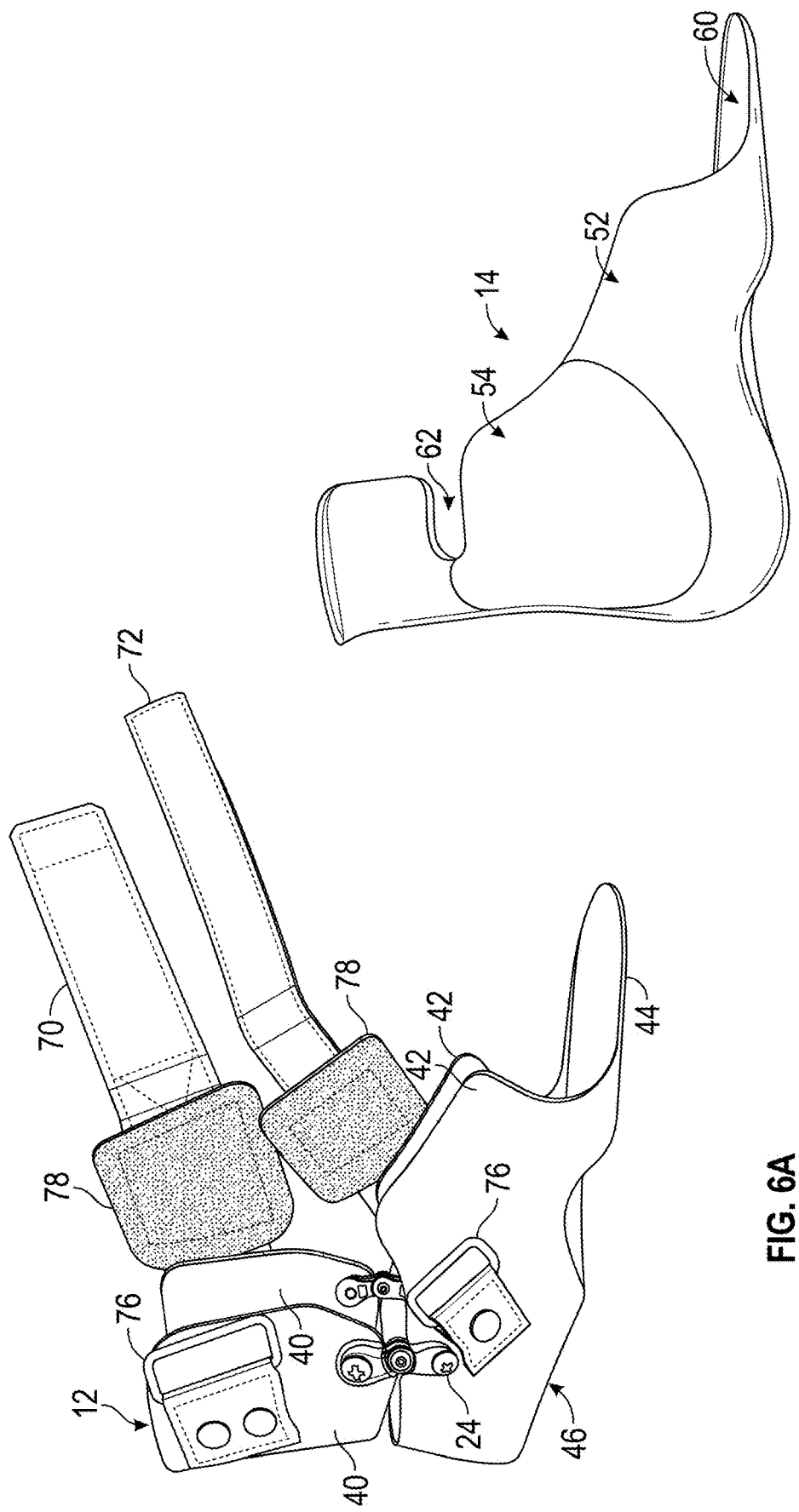
FIG. 6A is a side view of an outer boot of the ankle-foot orthosis illustrated in FIG. 2.
FIG. 6B is a side view of an inner boot of the ankle-foot orthosis illustrated in FIG. 2.

Referring to FIGS. 1-4, AFO 10 includes outer boot 12 and inner boot 14. Outer boot 12 includes upper portion 20 and lower portion 22. Upper portion 20 and lower portion 22 can be operably connected by at least one hinge assembly 24. As depicted in FIG. 4, upper portion 20 and lower portion 22 are generally operably connected by two hinge assemblies 24 positioned proximal user's ankle joint. In general, hinge assemblies 24 are positioned medially and laterally with respect to a user's ankle. In an embodiment, hinge assemblies 24 define an axis of rotation substantially aligned with the anatomical axis of rotation of the user's talocrural joint.

Referring to FIG. 4, upper portion 20 and lower portion 22 may include upper recesses 26 and lower recesses 28, respectively. Upper and lower recesses 26, 28 are generally adapted to receive a portion of hinge assembly 24. In particular, upper and lower recesses 26, 28 are generally sufficiently deep in relation to the thickness of hinge assembly 24 so as not to protrude beyond the inner surface of outer boot 12. In this manner, contact between inner boot 14 and hinge assemblies 24 can be minimized or eliminated, and hinge assembly 24 does not extend a significant distance beyond an outer surface of outer boot 12.

In alternative embodiments, hinge assembly 24 may be in the form of a joint 90, as depicted in FIGS. 15A-F. Joint 90 includes first member 92 and second member 94. First member 92 generally has structure, such as flanges 96, adapted to grasp second member 94. First and second member 92, 94 may be attached to outer boot 12 by any number of fastening members, such as, for example, rivets. In an embodiment, second member 94 defines aperture 98 such that flanges 96 clasp an end portion of second end 94 proximal aperture 98. The respective ends of first member 92 and second member 94 are thereby attached to each other at what becomes the central portion of joint 90 to form a pivoting single-axis hinge. By minimizing the number of moving parts, joint 90 can maintain a relatively thin profile, which enhance comfort, reduce overall weight and facilitate overall operability of AFO 10. In particular, joint 90 offers a streamlined profile that reduces obstruction and/or interference with a shoe or other footwear worn or donned by a user.

Figure 1:
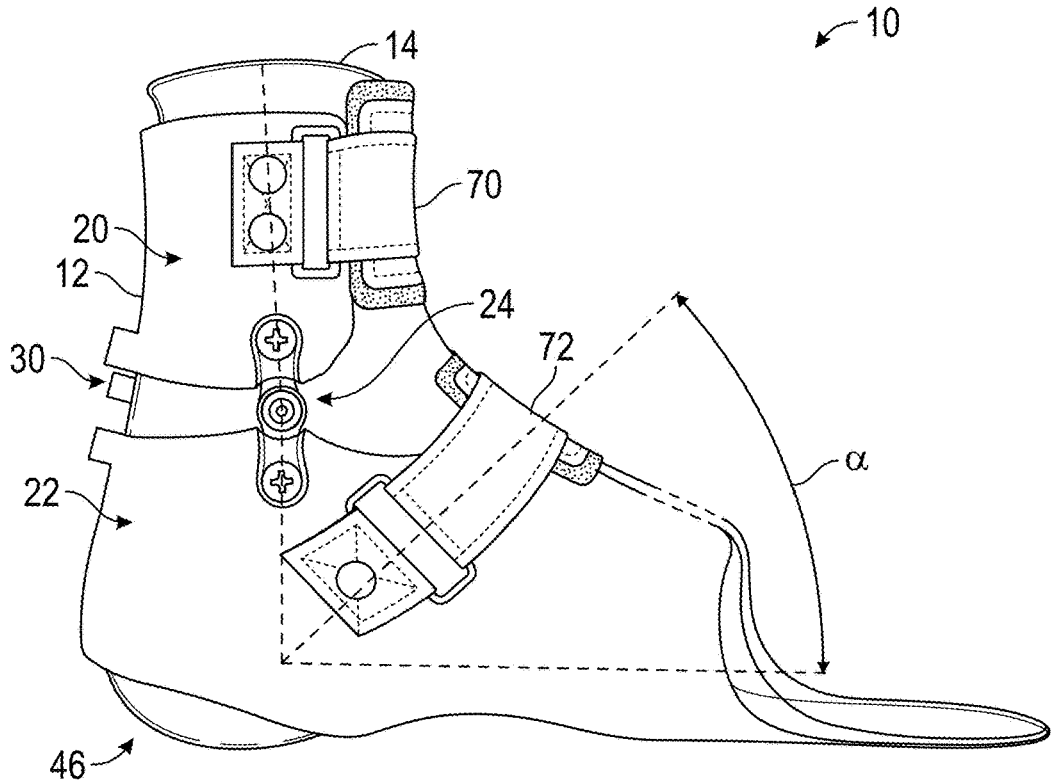
FIG. 1 is a side view of an embodiment of an ankle-foot orthosis.

Outer boot 12 may also include posterior stop 30, as shown in FIG. 1. Posterior stop 30 is generally adapted to limit a user's range of plantar flexion when fitted with AFO 10. Posterior stop 30 can be any number of stops known to one skilled in the art, such as, for example, the stop mechanisms described in U.S. Pat. No. 7,018,350, US 2003/0153852, US 2003/0153858, US 2003/0153858 and US 2003/0158506. In the embodiment shown in FIGS. 2-10, upper portion 20 and lower portion 22 of outer boot 12 may include complementary surfaces, such as upper and lower recess edges 32, 36 and upper and lower posterior edges 34, 38, that limit plantar flexion of a user fitted with AFO 10. In an embodiment, upper recess edges 32 of upper recesses 26 can be shifted into abutment with lower recess edges 36 of lower recesses 28. In another embodiment, upper portion 20 presents upper posterior edge 34 that can be shifted into abutment with lower posterior edge 38 of lower portion 22 in the sagittal plane.

Due to the rigidity of the material of outer boot 12, contact between upper recess edge 32 and lower recess edge 36, and/or contact between upper posterior edge 34 and lower posterior edge 38, substantially inhibits, or prevents, further plantar flexion of AFO 10. In an embodiment, outer boot 12 is constructed such that contact between upper recess edges 32 and lower recess edges 36 occurs simultaneously at medial and lateral locations of outer boot 12.

Referring to the embodiment illustrated in FIG. 2, upper portion 20 and lower portion 22 form an angle θ. Angle θ decreases during plantar flexion and increases during dorsiflexion. Plantar flexion is effectively limited, or stopped, when angle θ reaches its minimum, angle $\theta_{min}$. As the discussion below illustrates, the range of flexion permitted by AFO 10 and which is defined by $\theta_{min}$ can be varied by changing the configuration of various upper portion 20 and lower portion 22.

For embodiments of AFO 10 depicted in FIGS. 2-10, angle θ reaches angle $\theta_{min}$ when upper recess edges 32 abut with lower recess edges 36. For embodiments of AFO 10 as depicted in FIG. 1, angle θ reaches angle $θ_{min}$ when the stopping bumper and the bumper rest of posterior stop are in abutment. Therefore, when angle θ reaches angle $θ_{min}$, upper portion 20 cannot be further rotated posteriorly with respect to lower portion 22 and plantar flexion is effectively stopped.

Figure 7:
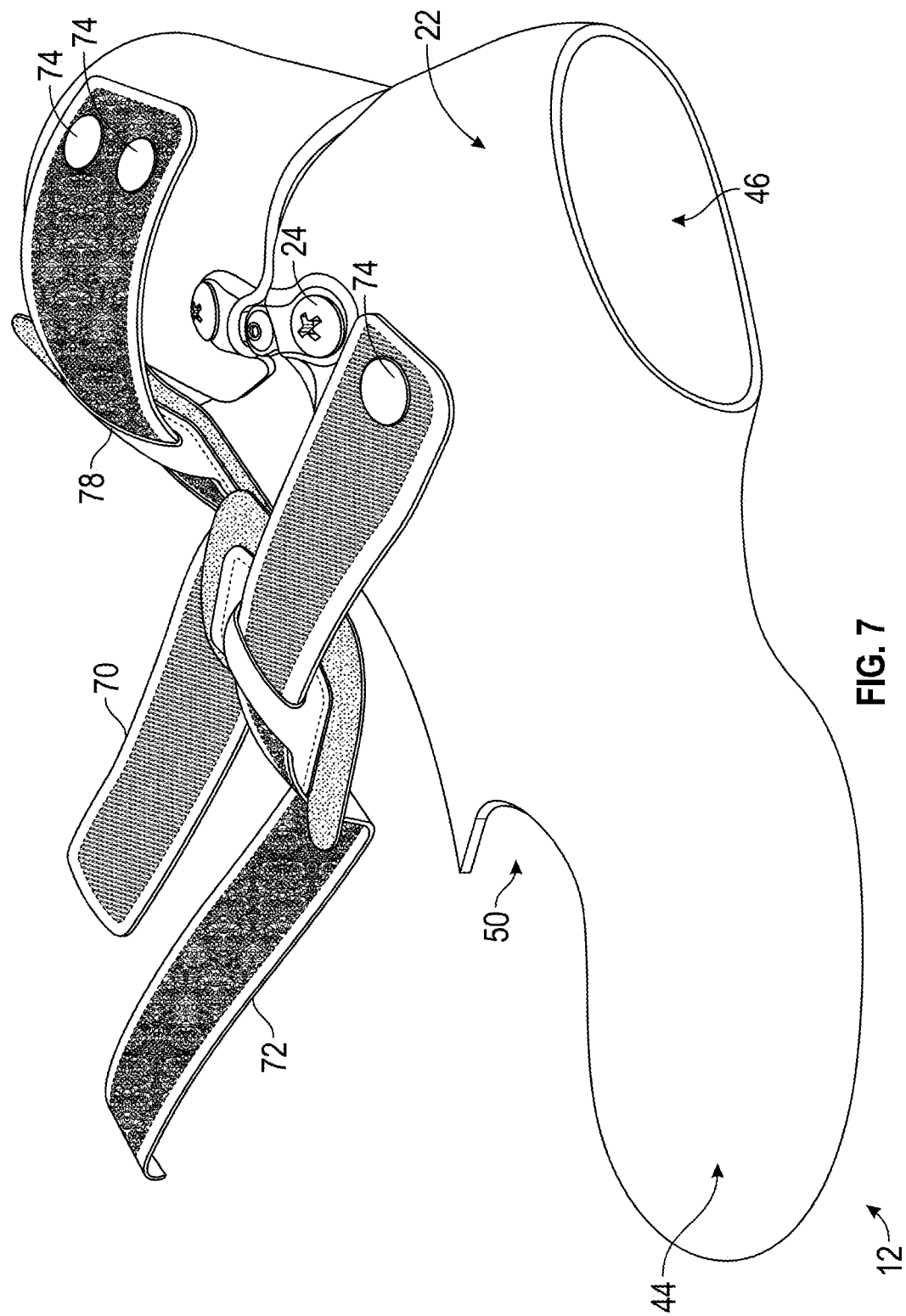
FIG. 7 is a bottom perspective view of an outer boot of the ankle-foot orthosis illustrated in FIG. 2.
Figure 8:
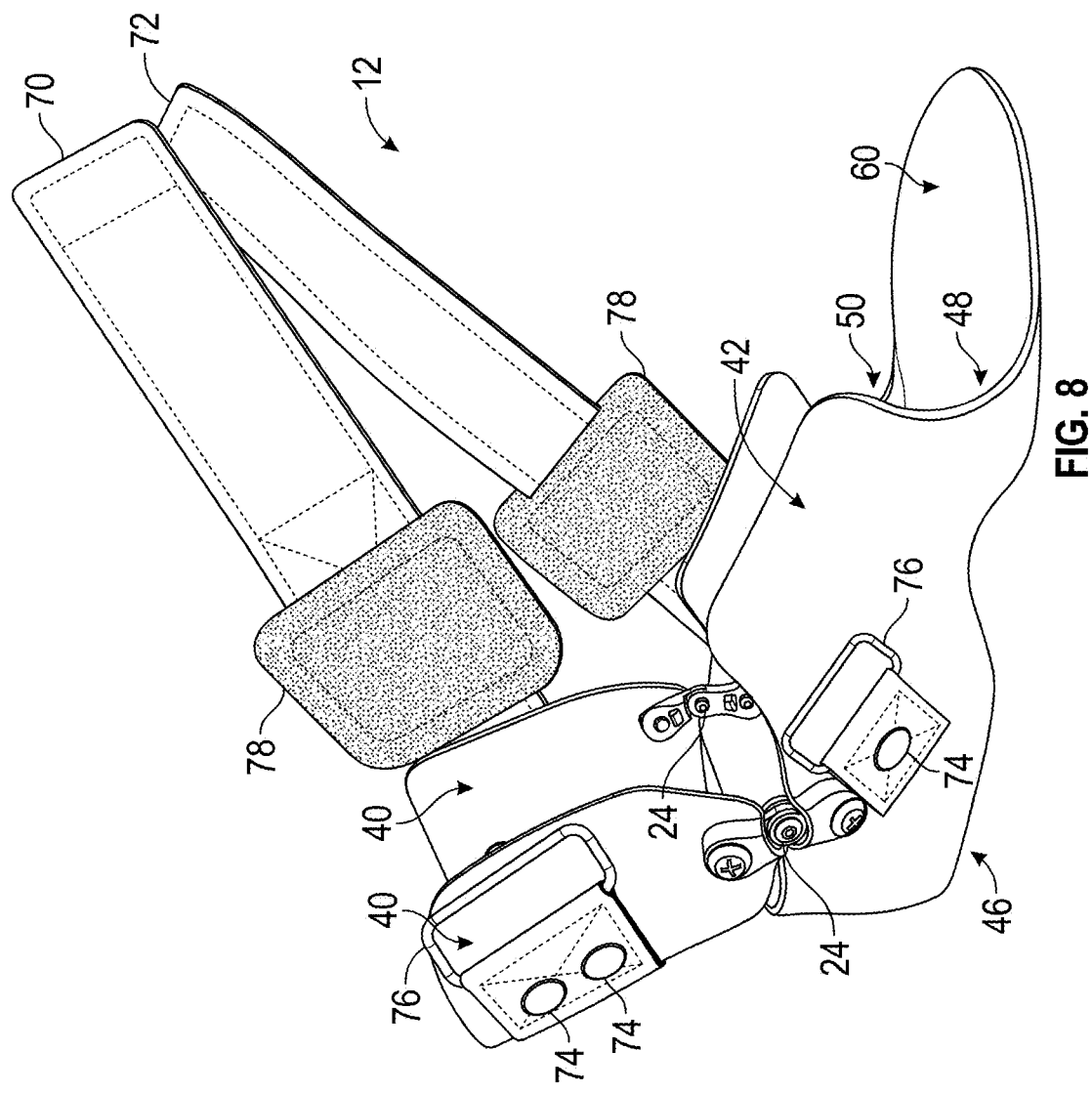
FIG. 8 is a top perspective view of the ankle-foot orthosis illustrated in FIG. 2.
Figure 9:
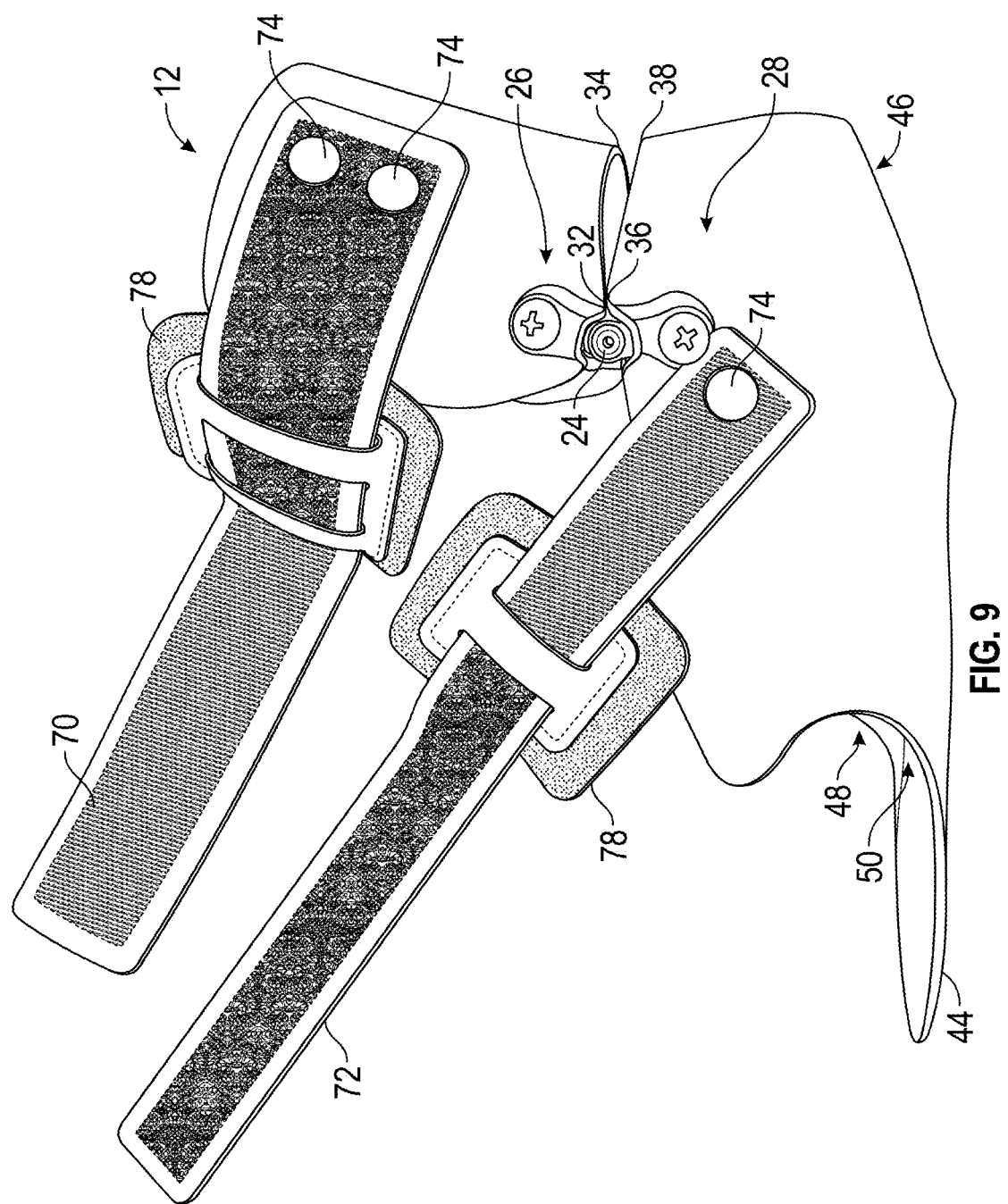
FIG. 9 is a side view of an outer boot of the ankle-foot orthosis illustrated in FIG. 2.
Figure 10:
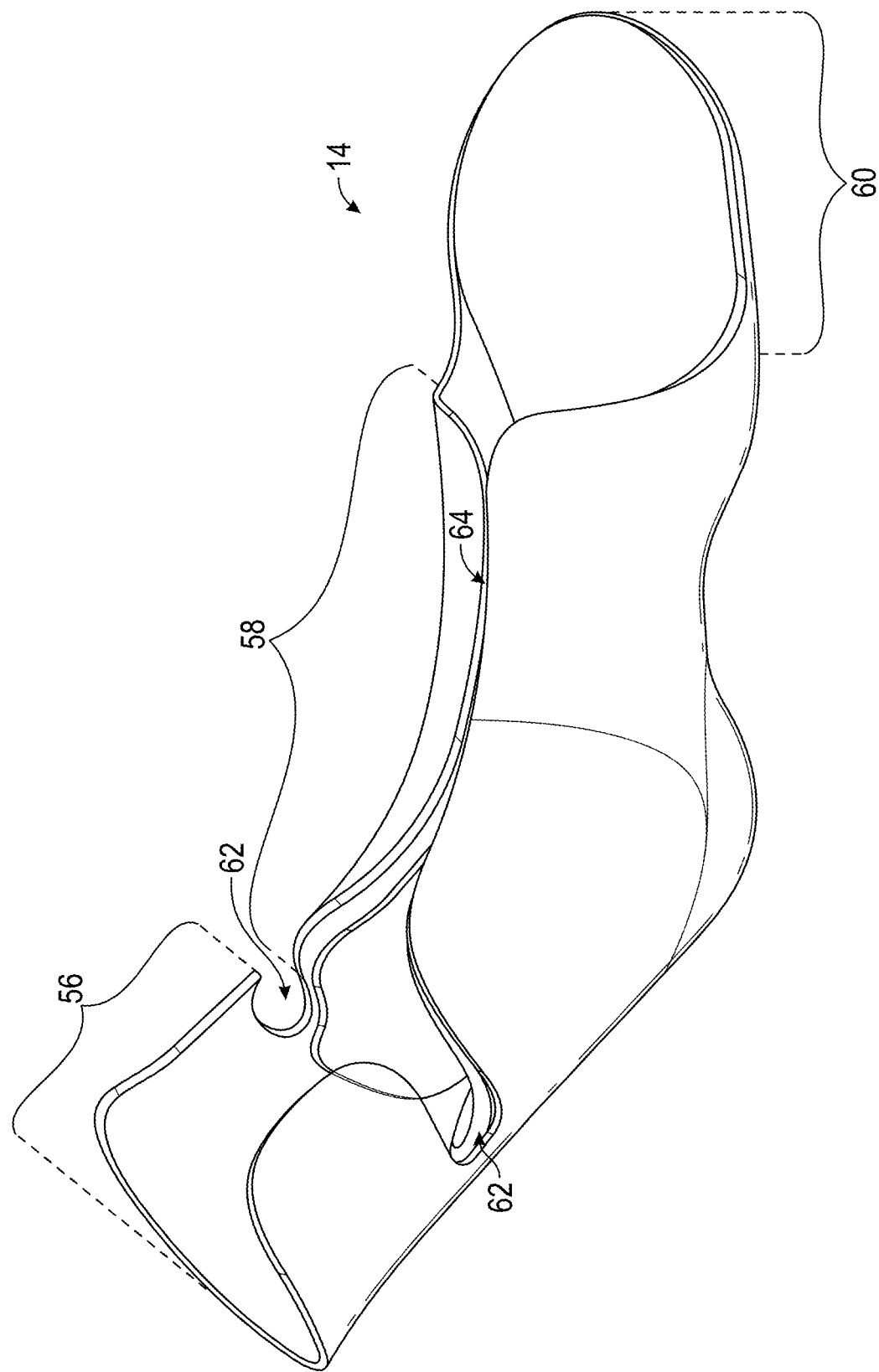
FIG. 10 is a top perspective view of an inner boot of the ankle-foot orthosis illustrated in FIG. 2.

Referring to FIGS. 5A, 6A and 7, outer boot 12 includes a number of features adapted to enhance overall comfort and functionality of AFO 10. Upper portion 20 includes upper forewalls 40 and lower portion 22 includes lower forewalls 42. Upper forewalls 40 and lower forewalls 42 allow outer boot 12 to substantially surround the ankle-foot region of a user while providing sufficient space for the insertion of inner boot 14. In particular, upper forewalls 40 extend partially around the anterior portion of the lower tibial region of the user's leg, while lower forewalls 42 extend partially around the superior/dorsum portion of the metatarsal region of the user's leg (i.e., a portion of the user's foot and lower portion of a user's ankle). In an embodiment, upper forewalls 40 extend approximately 45% to 75% around the lower tibial region of the user's leg, or approximately 60% around the lower tibial region of the user's leg, while lower forewalls 42 extend approximately 70% to 90% around the metatarsal region of the user's foot, or approximately 80% around the lower metatarsal region of the user's foot. In an embodiment, upper forewalls 40 define a gap of between approximately one inch (1") to approximately one and one-half inches (1½") around the lower tibial region of the user's leg, while lower forewalls 42 extend approximately one inch (1") to approximately one and one-half inches (1½") around the metatarsal region of the user's foot. As discussed below, the configuration of forewalls 40, 42 are particularly configured to achieve a desired a desired relationship with other components.

Lower portion 22 includes extension 44. Extension 44 generally extends distally from the base of lower portion 22 in a substantially transverse plane. In an embodiment, extension 44 extends sufficiently to support the phalangeal region, or toes, of a user's foot.

Upper portion 20 and lower portion 22 may be characterized by relief openings, or cutouts, to enhance comfort at anticipated pressure points and zones of AFO 10 and to augment motion control. As used herein, the term "cutout" refers to the general shape of a relief opening rather than to a process or method of forming the relief opening. In an embodiment, lower portion 22 defines heel opening 46. The size of heel opening 46 relative to size of lower portion 22 can vary, but is generally adapted to accommodate the heel of a user. Specifically, the heel of a user can protrude through heel opening 46 without causing impingement upon the region of the heel at or around heel opening 46 in lower portion 22. Including heel opening 46 in lower portion 22 substantially reduces and can eliminate a fulcrum effect that occurs at the heel strike when a user wears any type of AFO/boot or device that substantially immobilizes the user's foot in relation to the user's lower leg. This fulcrum effect is generally best illustrated when a user is walking in a rigid orthosis or ski boot. Specifically, this fulcrum effect occurs when a user enters heel-strike (first rocker) phase as the rigid portion of the outer boot 14 makes contact with the ground surface. The rotation about the contact point (i.e., heel) creates an anterior force that pulls at the knee joint, thereby causing the user to draw his or her knee forward at a faster than normal during the gait cycle, as the user transitions from first rocker of the stance phase to second rocker of the stance phase. The presence of heel opening 46 allows for a more fluid and normal transition from first rocker of the stance phase to second rocker of the stance phase for the user by reducing the anterior force pulling at the knee joint.

In an embodiment, lower portion 22 also defines inner cutout 48 and outer cutout 50. As with heel opening 46, the sizes of inner cutout 48 and outer cutout 50 can vary. In an embodiment, inner cutout 48 is sized to accommodate the area of a user's foot proximal the navicular and the outer cutout 50 is sized to accommodate the area of a user's foot proximal the fifth metatarsal. By decreasing pressure at or around the navicular and fifth metatarsal, inner cutout 48 and outer cutout 50, respectively, can reduce callusing around these areas.

Inner boot 14 is generally disposed intermediate outer boot 12 and user such that inner boot 14 functions, in part, as a liner for outer boot 12. In relation to outer boot 12, inner boot 14 is generally more dynamic in that it permits greater freedom of movement. Referring to FIGS. 5B and 6B, inner boot 14 includes first layer 52, and may include second layer 54 as well. Second layer 54 may be of a different material than first layer 52 so as to provide additional padding. As illustrated, second layer 54 (which may be made of padding) may be included in only a portion of inner boot 14. First layer 52 is generally a continuous piece of substantially flexible material that can be conformingly situated in the interior space defined by outer boot 12. As discussed below, first layer 52 of inner boot 14 generally helps to curtail movement. First layer 52 of inner boot 14 also stores and releases energy during the gait cycle to provide resistance, or a binding effect, as the user transitions from second rocker to third rocker of the stance phase. Second layer 54 generally enhances overall comfort by providing added cushioning at select pressure points.

Inner boot 14 includes vertical section 56, flexion section 58 and distal section 60. Vertical section 56 extends above flexion section 58 and substantially around Achilles region of user. Distal section 60 extends distally from flexion section toward the phalangeal region of a user's foot. Flexion section 58 substantially conforms to and surrounds the central portion of a user's foot and ankle. As shown in FIGS. 5B and 6B, a portion of vertical section 56 may be separated from flexion section 58 by upper opening 62. In an alternative embodiment, no upper opening 62 is present such that vertical section 56 is not separated from flexion section 58. Referring to FIG. 3, dorsal opening 64 divides flexion section 58 of inner boot 14 into outer portion 66 and inner portion 68. Dorsal opening 64 allows outer and inner portions 66, 68 to be separated so as to accommodate insertion of the user's foot in multiple positions. Once the user's foot is inserted, outer and inner portions 66, 68 of flexion section 58 substantially conform around metatarsal and talus region of the user's ankle. Preferably, inner boot 14 is sized and configured so that dorsal opening 64 will be carefully sized to help accommodate particular functions of AFO 10.

AFO 10 generally also includes a mechanism for securing outer boot 12 and inner boot 14 to the ankle-foot region of a user. Referring to FIGS. 1-9, AFO 10 includes upper strap 70 and lower strap 72. One skilled in the art will recognize that other tensioning devices could also be used without departing from the spirit or scope of the present invention, such as, for example, laces or ratcheting buckles.

Figure 11:
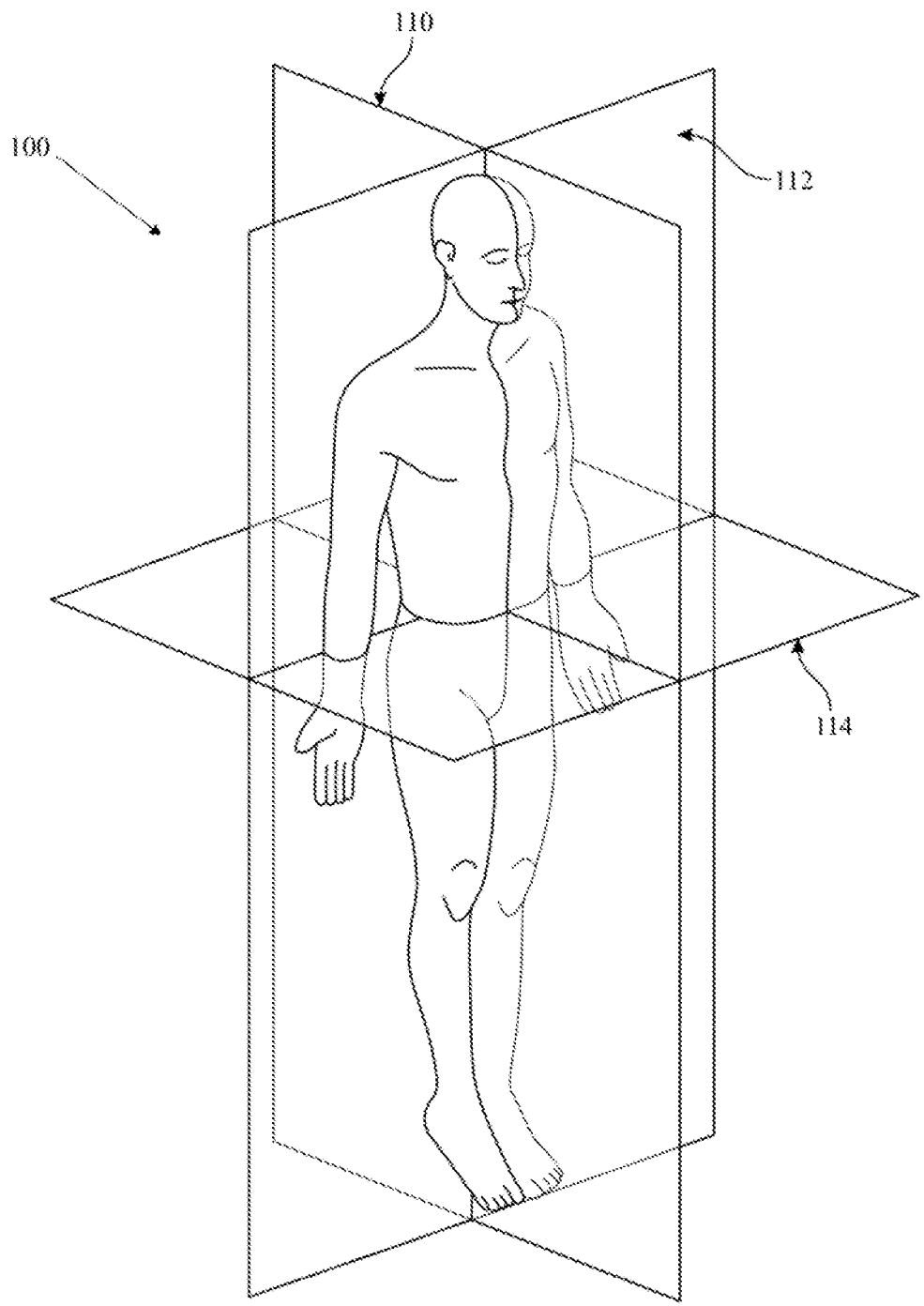
FIG. 11 is a diagram of the anatomical planes.
Figure 12:
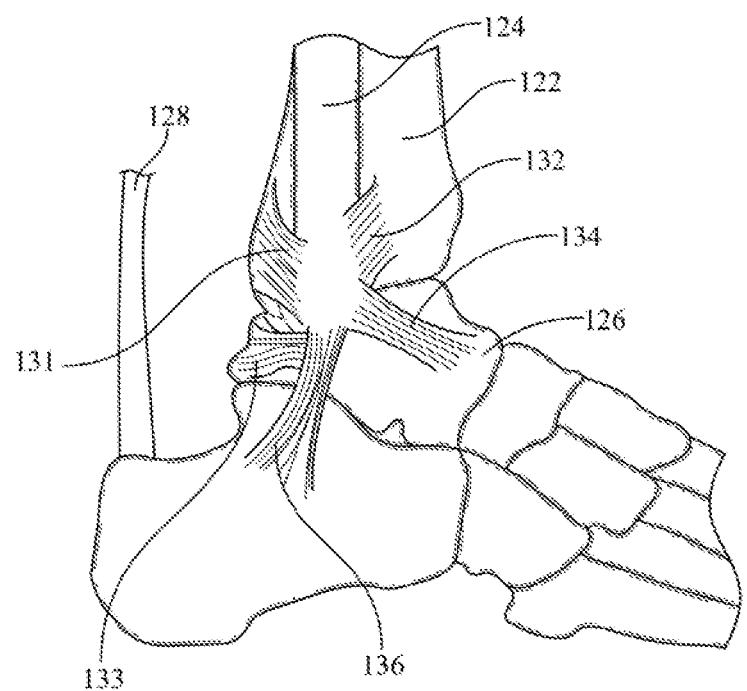
FIG. 12 is a diagram of the ankle-foot region.
Figure 13:
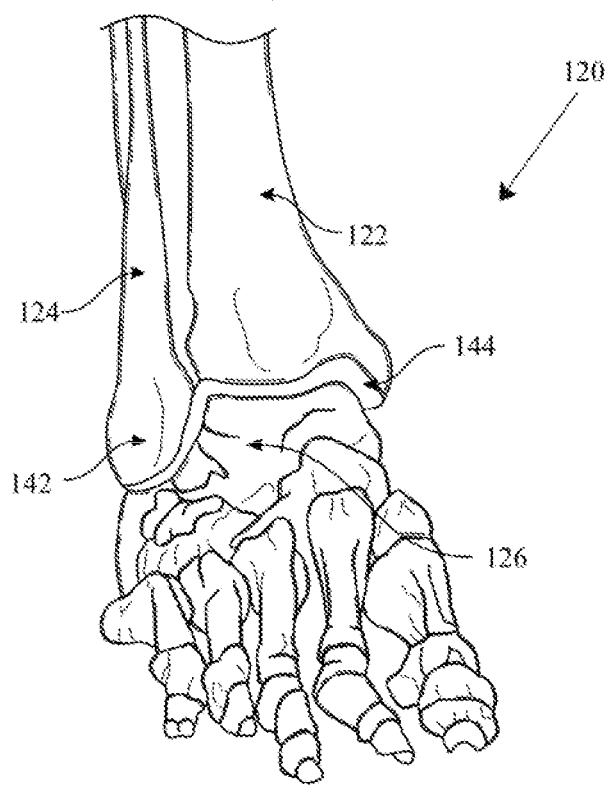
FIG. 13 is a diagram of the ankle joint.
Figures 14A, 14B:
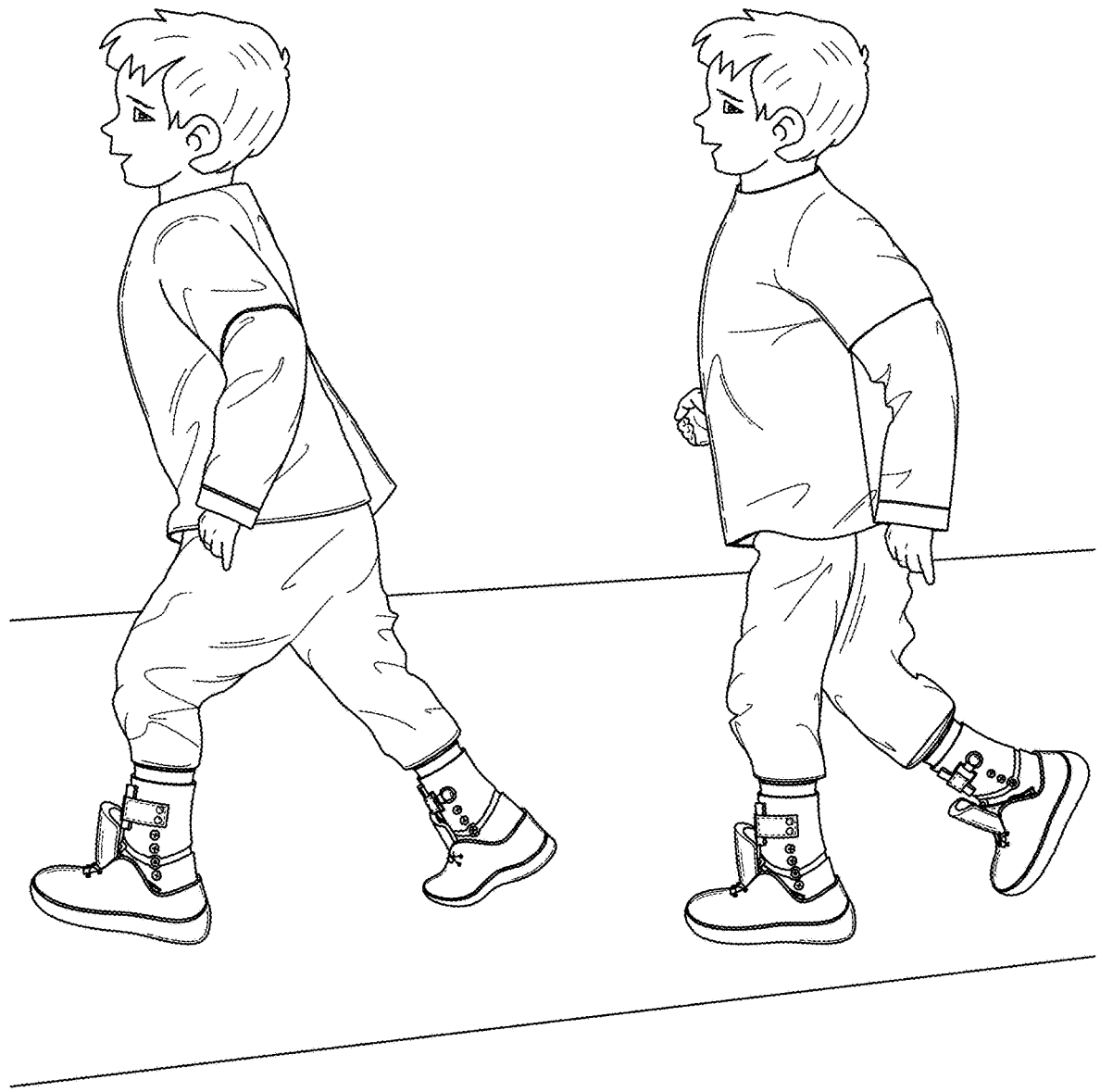
FIGS. 14A-D illustrate use of an embodiment of an ankle-foot orthosis during the gait cycle.
Figures 14C, 14D:

To provide further reference to the applicable anatomical structures, FIGS. 11-13 illustrate various well understood reference points. More specifically, FIG. 11 shows the Median/saggital plane 110, the frontal/coronal plane 112 and the transverse/horizontal plane 114 of the human body 100. Similarly, FIGS. 12 and 13 show the well-known components of the human ankle. As illustrated, the ankle 120 includes a tibia 122, fibula 124, talus 126, achilles tendon 128, posterior inferior tibiofibular ligament 131, anterior inferior tibiofibular ligament 132, posterior talofibular ligament 133, anterior talofibular ligament 134, and calcaneofibular ligament 136. Also shown is the lateral malleolus 142 and talocrural joint 144.

Upper and lower straps 70, 72 are secured to upper and lower portions 20, 22, respectively, such as by rivets 74. Each strap 70, 72 may be secured medially or laterally and with one or more rivets 74. As depicted in FIG. 7, upper strap 70 is secured to medial side of upper portion 20 with two rivets 74, while lower strap 72 is secured to medial side of lower portion 22 with one rivet 74. In an embodiment, lower strap 72 is positioned proximal the instep of the user.

To accommodate attachment of straps, upper and lower portions 20, 22 may include one or more attachment rings 76, such as metallic d-rings or other, similar hardware. Like upper and lower straps 70, 72, attachment rings can be secured to medial or lateral locations on upper and lower portions 20, 22 and with one or multiple with rivets 74. As shown in FIG. 2, upper strap 70 is pulled over dorsal opening 64, inserted through attachment ring 76 and pulled back over dorsal opening 64, thereby drawing upper forewalls 40 toward each other. Similarly, lower strap 72 is pulled over dorsal opening 64, inserted through attachment ring 76 and pulled back over dorsal opening 64, thereby drawing lower forewalls 40 toward each other. Referring to FIG. 1, upper strap 70 is positioned substantially parallel to the transverse plane and lower strap 72 is positioned at an angle α between approximately 30° and approximately 60° in relation to the transverse plane. In an embodiment, lower strap 72 is positioned at an angle α of approximately 45° in relation to the transverse plane.

Tensioned upper and lower straps 70, 72 can be secured in place by any number of methods. In an embodiment, tensioned upper and lower straps 70, 72 are secured in place with integrated hook-and-loop fasteners. Upper and lower straps 70, 72 may also include pads 78, as shown in FIGS. 2, 3, 5A, 6A, and 7-9. Pads 78 enhance user comfort by distributing the inward force of tensioned straps 70, 72 over a larger surface area. In generally, pads 78 are large enough such that when upper and lower straps 70, 72 are tensioned, a portion of the pads are positioned beneath the upper forewalls 42 of upper portion 20 and lower forewalls 42 of lower portion 22. Pads 78 may also be made from a softer material than the material used to construct upper and lower straps 70, 72. Pads 78 may also be made from a relatively stiff material to enhance other features of operability, such as storing energy, resisting buckling of inner boot 14 and further resisting undesirable movement at ankle-foot joint.

In an embodiment, pad 78 for upper strap 70 abuts pad 78 for lower strap 72 when upper and lower straps 70, 72 are tensioned and secured. Such abutment substantially reduces or eliminates buckling of the inner boot 14 when the user's tibia rotates over the foot during the transition from second rocker to third rocker of the stance phase of the gait cycle. In an alternative embodiment, AFO 10 utilizes a single pad 78 that can be tensioned by both upper and lower straps 70, 72. Since two separates pads 78 that are independently secured by upper and lower straps 70, 72 can migrate away from each other or be positioned incorrectly by a user, use of a single, elongated pad 78 can reduce the risk of unwanted buckling of inner boot 14. Use of a single pad can also reduce the number of pressure points in AFO 10 experienced by a user.

To achieve optimal functionality of AFO 12, outer boot 12 should be made from a relatively stiff material, while inner boot 14 should be made from a relatively elastic material. In an embodiment, outer boot 12 is made from a polypropylene material or copolymer material. The polypropylene material should be relatively stiff. The thickness of outer boot 12 can be in the range of approximately one-sixteenth of an inch (1/16") to approximately one-fourth of an inch (1/4"). In an embodiment, the thickness of outer boot 12 is approximately one-sixteenth of an inch (1/16"). Outer boot 12 can be vacuum-formed.

In an embodiment, inner boot 14 is made from an elastomer, such as a silicone-based orthoflex material. The thickness of inner boot 14 can be in the range of approximately one-sixteenth of an inch (1/16") to approximately one-half inch (1/2"). In an embodiment the thickness of inner boot 14 is approximately three-sixteenths of an inch (3/16"). Inner boot 14 can be formed through standard vacuum forming processes used to manufacture articles such as drape form, blister form and bubble form.

In an embodiment, joint 90 is made from plastic or a metallic material, such as steel or aluminum. The length of joint may be between one inch (1") and five inches (5"), or approximately 3.10 inches. The width of joint may be between 0.25 inches and 3 inches, or approximately 0.63 inches. In an embodiment, the ends of joint 90 are curved upwards such that joint 90 has the properties of a leaf spring.

AFO 10 can be used to treat a wide range of pathologies that cause lower extremity weakness of the dorsiflexors and plantarflexors at the ankle that result in an impaired gait. Embodiments of AFO 10 as described herein can be used to control and/or treat various combination of motions that include poor foot posture and sagittal plane deficits such as foot drop (swing phase). and foot slap (stance phase) recurvatum (hyperextension at the knee) and crouch-knee positions.

In particular, AFO 10 according to an embodiment of the present invention utilizes inner boot 14 seated inside articulated outer boot 12 to dynamically assist and resist users with transverse, sagittal and/or coronal plane comprise at the foot and ankle. Specifically, by achieving a fit that performs similarly to an external ligament, AFO 10 allows and assists dorsiflexion while also limiting plantar flexion and maintaining a neutralized or corrected alignment at the foot and ankle.

AFO 10 can also assist and resist forward movement. In particular, the combination of inner boot 14 made from a unitary piece of flexible material and rigid, articulated outer boot 12 effectively controls unwanted sagittal plane alignments (such as recurvatum, crouch or knee flexion instabilities) while creating a spring effect that can be directed. This spring effect substantially eliminates the need for stop motion. In contrast, a single-boot articulated AFO requires a plantarflexion stop and a single-boot solid ankle AFO provides sagittal plane stop motion for both plantar flexion and dorsiflexion. The combination of both a flexible inner boot and rigid outer boot allows a user to effectively control unwanted sagittal plane alignments such as recurvatum, crouch or knee flexion instabilities. Stated differently, the inner boot 14 is adapted to receive and substantially surround a foot of a user and to allow some level of flexion of the foot of the user about a flexion axis and the outer boot 12 is adapted to receive the inner boot and further help to control movement. Again, outer boot 12 has upper portion 20 and lower portion 22 hingeably coupled to one another. Upper portion 20 and lower portion 22 are less flexible than the inner boot 14. When in use, AFO 10 is rotatable between plantar-flexed and dorsiflexed positions, with an equilibrium position located there between. When in the equilibrium position the inner boot and the outer boot cooperate to hold a user's foot in a substantially static or neutral position. In the plantar-flexed position, the inner boot and the outer boot cooperate with one another to produce a force designed to urge the user's foot to the dorsiflexed position. Conversely, when in the dorsiflexed position, the inner boot and the outer boot create a force to urge the user's foot to plantar flexed position.

AFO 10 can thereby provide powered walking assistance in the sagittal plane while preventing unwanted end-range dorsiflexion and plantar flexion motion at the ankle during the stance phase of the gait cycle. This is achieved by establishing soft and hard zones that eliminate the push-pull effect during the at the end of the stance phase while still providing functional control of the lower limb, thereby enhancing ambulatory performance.

During swing phase, the user's foot and ankle are held in a prepositioned sagittal alignment. As the user achieves heel strike during first rocker of stance phase, heel opening 46 of outer boot 12 exposes the softer material of inner boot 14. This substantially reduces, or eliminates, anterior draw at the user's knee as the patient transitions to mid-stance, or second rocker position.

As a user transitions from second rocker to third rocker during stance phase, inner boot 14 decelerates dorsiflexion of the user's foot. Specifically, inner boot 14 resists tibial progression over the foot of the user as the material of inner boot loads. This, in turn, prevents foot slap and enhances single-limb stance stability, while one or more pads 78 impede or substantially eliminate buckling of inner boot 14. In addition, the deformation of inner boot 14 that occurs during the initial transition from second rocker to third rocker causes inner boot 14 to store elastic energy. In addition, extension 44 is deformed, thereby also creating stored energy. Elastic energy stored by inner boot 14 and extension 44 is then released at the end of the transition from second rocker to third rocker as the heel, and later the toes, of the user are lifted off the ground surface. This release of elastic energy by inner boot 14 provides plantar flexion-power assistance as the user transitions from stance phase to swing phase, facilitating longer step lengths and normal foot clearance. The power generated by AFO 10 during third rocker phase thereby produces a more natural stepping motion and step lengths even accommodating jumping and/or running gaits, such as depicted in FIGS. 14A-D.

In practice, AFO 10 can be pre-positioned when obtaining a negative cast or during the modification or fitting process with respect to a user's limb in a desired sagittal alignment to optimize control of the limb. For example, if a user presents an undesirable low-tone crouch knee position, AFO 10 can be positioned such that upper portion 20 defines a substantially vertical axis. In contrast, if the user has a hyperextended knee, upper portion 20 can be positioned at an acute angle in relation to the transverse plane to oppose the compromised postural alignment of the hyperextended knee.

Various embodiments of the invention have been described above for purposes of illustrating the details thereof and to enable one of ordinary skill in the art to make and use the invention. The details and features of the disclosed embodiment(s) are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. An ankle-foot orthosis for a lower extremity comprising:
an inner boot formed of an elastomer configured to have a selected level of elasticity in both tension and compression, the inner boot configured to receive and closely surround an ankle-foot region of a foot of a user, the inner boot being formed of a continuous piece of substantially flexible material having a thickness in the range of approximately one-sixteenth of an inch to approximately one-half an inch and being configured to store and release energy during a gait cycle;
an outer boot formed from a substantially stiff material and being adapted to substantially surround the ankle-foot region of the user while also receiving the inner boot such that the inner boot is seated inside the outer boot and extends above the outer boot during use of the ankle-foot orthosis, the outer boot having an upper portion and a lower portion hingedly coupled to one another, the upper and lower portions of the outer boot being more rigid than the inner boot, and
a tensioner coupled to the outer boot movable between a closed position and an open position, wherein, when in the closed position, the tensioner, outer boot and inner boot are configured to contain the foot so that the ankle-foot orthosis will move with the foot;
wherein the inner boot is seated within the outer boot such that when the foot of the user is contained within the ankle-foot orthosis, the inner boot is configured to provide powered walking assistance to the user during a gait cycle, such that:
the ankle-foot orthosis is rotatable along the sagittal plane between plantar-flexed and dorsiflexed positions, with an equilibrium position centrally located there between, and wherein;
when in the equilibrium position, the inner boot and the outer boot are configured to cooperate with one another to hold the foot in a substantially static position when no competing forces are being applied by the user;
when in the plantar-flexed position, the inner boot and the outer boot are configured to cooperate to urge the foot to dorsiflex; and
when in the dorsiflexed position, the inner boot and the outer boot are configured to cooperate to urge the foot to plantar flex.

2. The ankle-foot orthosis of claim 1, wherein the outer boot includes a hinge coupling the upper portion to the lower portion such that the upper portion is rotatable in relation to the lower portion.

3. The ankle-foot orthosis of claim 2, wherein:
the upper portion presents an upper posterior edge and the lower portion presents a lower posterior edge; and
when the ankle-foot orthosis is in the plantar-flexed position, the upper posterior edge and the lower posterior edge abut one another and are configured to substantially limit further plantar flexion by the user.

4. The ankle-foot orthosis of claim 2, wherein:
the upper portion defines an upper recess presenting an upper recess edge and the lower portion defines a lower recess presenting a lower recess edge, the upper and lower recesses adapted to receive a hinge assembly; and
when the ankle-foot orthosis is in the plantar-flexed position the upper recess edge and the lower recess edge abut one another and substantially limit further plantar flexion by the user.

5. The ankle-foot orthosis of claim 1, wherein the tensioner is a first tensioner coupled to the upper portion, and the ankle-foot orthosis further comprises:
a second tensioner coupled to the lower portion;
wherein the first and second tensioners are configured to removably secure the ankle-foot orthosis to the foot of the user and contain the foot within the ankle-foot orthosis.

6. The ankle-foot orthosis of claim 5, wherein:
the first tensioner is tensionable substantially parallel to a transverse plane; and
the second tensioner is tensionable at an angle of between approximately 40° and approximately 50° in relation to the transverse plane.

7. The ankle-foot orthosis of claim 6, wherein the inner boot has a dorsal opening, and wherein:
the first tensioner comprises a first strap including a first pad;
the second tensioner comprises a second strap including a second pad; and
wherein the first and second pads are configured to capture the inner boot and control a size of the dorsal opening formed in the inner boot.

8. The ankle-foot orthosis of claim 1, wherein the outer boot defines an opening adapted to receive a heel of the user.

9. The ankle-foot orthosis of claim 1, wherein the outer boot includes a first cutout which is configured to expose a first region of the foot proximal the navicular and a second cutout which is configured to expose a second region of the foot proximal the fifth metatarsal.

10. The ankle-foot orthosis of claim 1, wherein the outer boot includes an extension adapted to support the toes of the user, the extension being resiliently flexible to propel the foot of the user from a third rocker position to swing phase.

11. The ankle-foot orthosis of claim 1, wherein the outer boot is configured to resist movement of the foot of the user in a transverse plane.

12. An ankle-foot orthosis for a lower extremity comprising:
an inner boot configured to receive and substantially surround an ankle-foot joint of a foot of a user, the inner boot being formed of an elastomer configured to allow flexion of the ankle-foot joint of the user while also providing a predetermined level of resistance in both tension and compression, wherein the predetermined level of resistance is dependent upon a selected level of elasticity and a selected thickness of the inner boot, the inner boot being formed of a continuous piece of substantially flexible material having a thickness in the range of approximately one-sixteenth of an inch to approximately one-half an inch and being configured to store and release energy during a gait cycle;
an outer boot formed from a substantially stiff material and being adapted to receive the inner boot such that the inner boot is seated inside the outer boot and extends above the outer boot during use of the ankle-foot orthosis, the outer boot comprising an upper portion and a lower portion hingedly coupled to one another;
a first tensioner coupled to the upper portion of the outer boot and tensionable substantially parallel to a transverse plane; and
a second tensioner coupled to the lower portion of the outer boot and tensionable at an angle of between approximately 40° and approximately 50° in relation to the transverse plane, wherein the first and second tensioners are configured to control a dimension of a dorsal opening formed in the inner boot;
wherein:
the outer boot defines an opening adapted to receive a heel of the user and includes a first cutout which is configured to expose a first region of the foot proximal the navicular and a second cutout which is configured to expose a second region of the foot proximal the fifth metatarsal;
wherein the ankle-foot orthosis is rotatable along the sagittal plane between plantar-flexed and dorsiflexed positions, with an equilibrium position centrally located there between, and, when the ankle-foot joint of the user is contained within the inner boot and the inner boot is seated within the outer boot, the combination of the inner boot and the outer boot is configured to provide powered walking assistance to the user during a gait cycle such that;
when in the equilibrium position, the inner boot and the outer boot are configured to cooperate with one another to hold the foot of the user in a substantially static position;
when in the plantar-flexed position, the inner boot and the outer boot are configured to cooperate with one another to urge the foot to dorsiflex; and
when in the dorsiflexed position, the inner boot and the outer boot are configured to cooperate with one another to urge the foot to plantar-flex.

13. The ankle-foot orthosis of claim 12 wherein the upper portion defines an upper recess presenting an upper recess edge and the lower portion defines a lower recess presenting a lower recess edge, the upper and lower recesses adapted to receive a hinge assembly; and when the ankle-foot orthosis is in the plantar-flexed position the upper recess edge and the lower recess edge abut one another and are configured to substantially limit further plantar flexion by the user.

* * * * *